United States Patent
Borgman et al.

(10) Patent No.: US 11,529,346 B2
(45) Date of Patent: Dec. 20, 2022

(54) VAGINAL GEL

(71) Applicant: National Medical Supply, LLC, Las Vegas, NV (US)

(72) Inventors: Robert J. Borgman, Mundelein, IL (US); James E. Juul, Wauconda, IL (US)

(73) Assignee: National Medical Supply, LLC, Las Vegas, NV (US)

( * ) Notice: Subject to any disclaimer, the term of this patent is extended or adjusted under 35 U.S.C. 154(b) by 45 days.

(21) Appl. No.: 16/904,678

(22) Filed: Jun. 18, 2020

(65) Prior Publication Data
US 2021/0393619 A1    Dec. 23, 2021

(51) Int. Cl.
| | | |
|---|---|---|
| *A61K 31/496* | (2006.01) | |
| *A61K 9/06* | (2006.01) | |
| *A61K 9/00* | (2006.01) | |
| *A61K 47/38* | (2006.01) | |
| *A61K 31/4164* | (2006.01) | |

(52) U.S. Cl.
CPC .......... *A61K 31/496* (2013.01); *A61K 9/0034* (2013.01); *A61K 9/06* (2013.01); *A61K 31/4164* (2013.01); *A61K 47/38* (2013.01)

(58) Field of Classification Search
CPC .................................................. A61K 31/496
USPC .................................................. 514/254.07
See application file for complete search history.

(56) References Cited

U.S. PATENT DOCUMENTS

| | | | | |
|---|---|---|---|---|
| 4,837,378 A | * | 6/1989 | Borgman | A61K 9/0014 424/78.05 |
| 5,840,744 A | | 11/1998 | Borgman | |
| 6,913,759 B2 | * | 7/2005 | Borgman | A61K 9/0034 424/407 |
| 10,398,692 B2 | | 9/2019 | Borgman et al. | |
| 2003/0180366 A1 | * | 9/2003 | Kirschner | A61P 31/18 424/489 |
| 2004/0151774 A1 | * | 8/2004 | Pauletti | A61P 25/04 424/488 |
| 2006/0093675 A1 | * | 5/2006 | Ebmeier | A61K 9/0034 514/398 |

FOREIGN PATENT DOCUMENTS

| | | | | |
|---|---|---|---|---|
| WO | 9955333 | | 11/1999 | |
| WO | WO 1999/055333 | * | 11/1999 | .......... A61K 31/415 |
| WO | 2005087270 A1 | | 9/2005 | |
| WO | WO 2005087270 | * | 9/2005 | ............. A61K 45/06 |

OTHER PUBLICATIONS

Tolman, Antimicrobial Agents and Chemotherapy, Jun. 1986, p. 986-991.*
Sood, Infectious Diseases in Obstetrics and Gynecology 8:240-243 (2000).*
Cunningham, F.E. et al., Pharmacokinetics of intravaginal metronidazole gel. J Clin Pharmacol. 1994;34(11):1060-1065.
Lamp, K.C., et al., Pharmacokinetics and pharmacodynamics of the nitroimidazole antimicrobials. Clin Pharmacokinet. 1999;36(5):353-373.

* cited by examiner

*Primary Examiner* — Nizal S Chandrakumar
(74) *Attorney, Agent, or Firm* — Olson & Cepuritis, Ltd.

(57) ABSTRACT

A composition having gel-like consistency contains metronidazole, terconazole, a physiologically acceptable thickener and water. The composition is useful for treating bacterial vaginosis as well as vulvovaginal candidiasis.

5 Claims, 1 Drawing Sheet

VAGINAL GEL

FIELD OF INVENTION

The invention relates compositions and treatments for bacterial vaginal infections.

BACKGROUND OF INVENTION

Bacterial vaginosis (BV) is one of the most common vaginal disorders in women of reproductive age. BV is characterized by a shift in the vaginal flora whereby the normal populations of vaginal Lactobacilli decline and are replaced by an overgrowth of facultative and anaerobic bacteria such as Gardnerella vaginalis, Atopobium, Prevotella, Bacteroides, Peptostreptococcus and Mobiluncus species.

BV is associated with an increased volume of vaginal discharge having a foul, fishy odor. Vaginal pH is elevated from the normal range (pH 3-4) to values greater than about pH 4.5. The odor and elevated pH are caused by a high level of amines, most notably trimethylamine, in the vagina. These amines are volatilized when the pH is raised, for example, as with addition of KOH or interaction with semen.

Typically, a clinical diagnosis of BV is made if three or more of the following four clinical criteria (known as Amsel's criteria) are present: (1) abnormal discharge; (2) a pH value greater than or equal to about 4.5; (3) a "fishy" amine odor upon the addition of 10% KOH to discharge; (4) presence of epithelial clue cells (where the cell borders are obscured by bacteria) in an amount greater than or equal to about 20% of vaginal epithelial cells on microscopic examination of vaginal fluid wet mount.

BV is generally treated with antibacterials that have activity against anaerobic organisms, for example metronidazole or clindamycin. Metronidazole is commonly used and is available both in oral tablets and vaginal creams and gels. Vaginal dosage forms are often preferred because they limit systemic exposure to the drug, while providing a high local concentration of antibacterial. For example, typical oral metronidazole doses used for the treatment of BV are 500 milligrams twice daily for seven days, while metronidazole 0.75% vaginal gel is generally used in doses of 5 grams of gel containing 37.5 milligrams of metronidazole once daily for five days. The pharmacokinetic profile following administration of a single dose of metronidazole 0.75% gel containing 37.5 milligrams of metronidazole shows far lower blood levels (Cmax 237 ng/ml and AUC 4,977 ng*hr/ml), compared to that following a standard oral 500 milligram tablet, (Cmax 12,785 ng/ml and AUC 133, 395 ng*hr/ml)

Vulvovaginal candidiasis (VVC), also known as yeast vaginitis, is another common vaginal infection characterized by the overgrowth of yeasts. The primary symptoms of VVC are itching, burning and irritation of the vagina and/or vulva. The associated signs include erythema, edema and excoriation. Candida albicans is the causative pathogen in the majority of cases. Candida organisms may be cultured or seen on wet mount examination of vaginal fluid.

VVC is generally treated with azole antifungals that have activity against Candida species. Dosage forms include oral triazoles such as fluconazole, and vaginal creams or suppositories containing azoles such as miconazole, clotrimazole, and terconazole.

In some instances, female patients suffer from BV and vulvovaginal candidiasis (VVC) concurrently. Microbiologic studies have indicated that up to 15% of women who experience a vaginal infection are co-infected with BV organisms along with yeast such as Candida. In such cases successful treatment requires the use of more than one medication—an antibacterial to treat BV and antifungal to treat the VVC. Often this treatment consists of an oral dosage form, such as oral metronidazole, and a vaginal dosage form, such as miconazole cream.

For locally acting antibacterial and antifungal drugs used to treat vaginal infections, the extent and timing of release of the drug from the formulation is important. Especially when considering drugs that are readily absorbed across the vaginal mucosa, such as metronidazole, the pharmacokinetic profile reflects, to some extent, the degree and timing of drug release from the formulation.

For example, two commercially available water-based vaginal gels used for the treatment of BV show similar pharmacokinetic profiles, even though they contain different amounts of drug per dose. A 1.3% metronidazole vaginal gel, containing 65 mg of metronidazole per dose, produces blood levels (Cmax 239 ng/ml and AUC 5,434 ng*hr/ml), which are almost identical to 0.75% metronidazole gel containing 37.5 mg per dose. (Cmax 237 ng/ml and AUC 4,977 ng*hr/ml), The present invention provides a unique gel formulation of metronidazole and terconazole for treating BV as well as VCC. Unexpectedly, when the antifungal terconazole is formulated with the antibacterial metronidazole, this combination exhibits enhanced antibacterial bioavailability when compared to the antibacterial formulation alone. This enhanced bioavailability has also been shown to be advantageous in the treatment of By in women who have both BY and VVC when compared to the antibacterial alone.

SUMMARY OF INVENTION

A therapeutic composition, such as a vaginal gel, for treating bacterial vaginosis (BV) and providing enhanced bioavailability of metronidazole includes, in addition to metronidazole, terconazole, a physiologically acceptable thickener, and a buffer system which provides a buffered pH value for the composition in the range of about 3.75 to about 4.25. The respective mole ratio of metronidazole to terconazole preferably is in the range of about 3 to about 4, more preferably about 3.5.

DESCRIPTION OF PREFERRED EMBODIMENTS

Definitions

Figure 1:
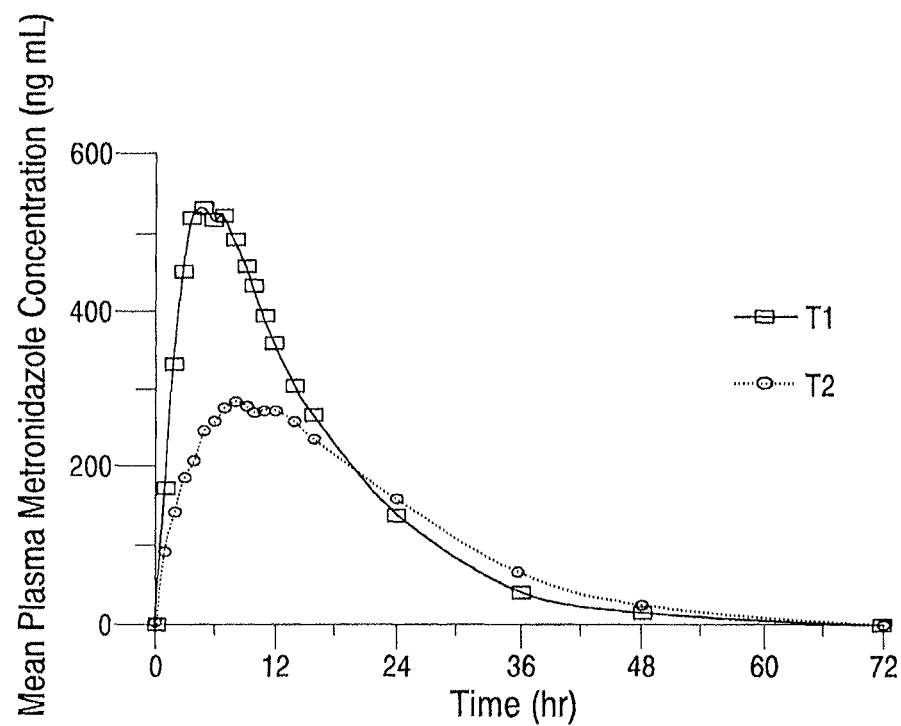
FIG. 1 is a graph showing bioavailability of metronidazole alone and in a combination with terconazole in a gel-like carrier.

The term "buffer system" or "buffer" as used herein and in the appended claims refer to a solvent agent or agents which, when dissolved in water, stabilize the resulting solution against a major change in pH when acids or bases are added. A preferred buffer system for purpose of the present invention is a citric acid—sodium citrate system.

The terms "unit dose" or "unit dosage form" as used herein and in the appended claims refers to physically discrete units of the present composition suitable for administration to human female subjects. Each unit contains a predetermined amount of metronidazole and terconazole calculated to produce the desired therapeutic effect. The unit dosage form to be administered to any given patient is dictated by and dependent on (1) the particular therapeutic effect to be achieved (2) and the release rate of the active agents from the particular composition utilized.

The term "vagina" as used herein and the appended claims is inclusive of the vaginal region generally, including the vulva and the cervix.

The quantity of the therapeutic composition introduced intravaginal, for treatment of bacterial vaginosis (BV) can vary widely, depending on age and physical condition of the patient, the extent of affliction, frequency of administration, and the like factors.

The active ingredients in the present therapeutic compositions are metronidazole (1-(2-hydroxyethyl)-2-methyl-5-nitroimidazole; M.W.171.156 g/mol) and terconazole cis-1-[p-[[2-(2,4-Dichlorophenyl)-2-(1H-1,2,4-triazole-1-ylmethyl)-1,3-dioxolan-4-yl]methoxy]phenyl]-4-isopropylpiperazine; M.W. 532.462 g/mol). The terms "metronidazole" and "terconazole" as used herein and appended claims also includes analogs and derivatives thereof that exhibit therapeutic activity when used as described herein.

Metronidazole and terconazole both are commercially available compounds.

Suitable physiologically acceptable thickeners are cellulose derivatives such as hydroxypropyl methyl cellulose, hydroxy ethyl cellulose, sodium carboxymethyl cellulose, as well as the polyacrylic acid polymers cross-linked with polyacrylic acid polymers and commercially available from Lubrizol Corporation, Cleveland Ohio under the designations CARBOPOL 934, CARBOPOL 940, CARBOPOL 950, and the like.

The present compositions can also contain optional preservatives, chelating agents, a cosolvent, viscosity stabilizes, and the like.

Suitable preservatives are the lower alkyl esters of para-hydroxybenzoic acid, e.g., methyl paraben, propyl paraben, and the like, sodium benzoate, ethylene diamine tetraacetic acid (EDTA), and the like.

Suitable cosolvants are dihydric and polyhydric alcohols such as propylene glycol, glycerin, sorbitol, 1, 2, 6-hexane triol, and the like.

A suitable viscosity stabilizer is methionine, and the like. In the gel-like compositions embodying the invention metronidazole and terconazole are present in a respective mole ratio in the range of about 3 to about 4, preferably about 3.5.

The concentration of metronidazole present in the compositions is at least about 0.5 weight percent, based on the weight of the composition, preferably in the range of about 0.75 weight percent to about 1 percent weight, and more preferably about 0.9 weight percent.

The concentration of terconazole present in the composition is at least about 0.4 weight percent, based on the weight of the composition, preferably in the range of about 0.6 weight percent to about 1.2 weight percent, more preferably about 0.8 weight percent.

The quality of metronidazole contained in a unit dose generally is at least about 20 milligrams and not more than about 100 milligrams. A preferred unit dose of metronidazole in a gel vehicle is in the range of about 20 to about 60 milligrams, more preferably about 45 milligrams.

The quantity of terconazole contained in a unit dose generally is at least about 16 milligrams and not more than about 80 milligrams. A preferred unit dose of terconazole in the gel vehicle is in the range of about 16 to about 50 milligrams, more preferably about 40 milligrams.

Experimental compositions having the composition shown in Table 1, below, were prepared to determine bioavailability of metronidazole as well as terconazole from single entity gels as well as from a combination gel. These experimental gels were also used to treat women with mixed (concomitant) BV and VVC. The indicated percentages in Table 1 are percentages by weight.

TABLE 1

| Experimental Compositions | | | |
|---|---|---|---|
| | Metronidazole + terconazole gel (T1) | Metronidazole-only gel (T2) | Terconazole-only gel (T3) |
| Active ingredients | | | |
| Metronidazole | 0.9% | 0.9% | 0 |
| Terconazole | 0.8% | 0 | 0.8% |
| Inactive ingredients | | | |
| Hypromellose, 2208, USP | 2.5% | 2.5% | 2.5% |
| Propylene glycol, USP | 3% | 3% | 3% |
| l-Methionine, USP | 0.18% | 0.18% | 0.18% |

TABLE 1-continued

Experimental Compositions

| | Metronidazole + terconazole gel (T1) | Metronidazole-only gel (T2) | Terconazole-only gel (T3) |
|---|---|---|---|
| Methylparaben, NF | 0.08% | 0.08% | 0.08% |
| Propylparaben, NF | 0.02% | 0.02% | 0.02% |
| EDTA | 0.05% | 0.05% | 0.05% |
| Citric acid, USP | 0.43% | 0.43% | 0.43% |
| Sodium citrate, USP | QS to pH 4.0 | QS to pH 4.0 | QS to pH 4.0 |
| Purified water, USP | QS to 100% | QS to 100% | QS to 100% |

A single dose crossover bioavailability study was conducted in healthy female volunteers using the preparations shown in Table 1, above. Five grams of each preparation was filled into a vaginal applicator and administered to each subject. Each applicator corresponded to 45 milligrams of metronidazole, or 40 milligrams of terconazole, or 45 milligrams of metronidazole and 40 milligrams of terconazole. Twenty-four (24) subjects were enrolled in the study of which twenty-one (21) completed the study. Subjects were housed from at least 12 hours prior to drug administration until 24 hours thereafter. Thereafter, subjects reported to the study facility at 36 hours, 48 hours, and 72 hours. The subjects were treated with each of these gels according to a randomization schedule.

Plasma samples were obtained from the subjects within 90 minutes prior to dose administration (0 hr) and post-dose at hourly intervals starting with one hour after dose administration for the first twelve hours and thereafter at 14 hrs, 16 hrs, 24 hrs, 36 hrs, 48 hrs and 72 hrs in each study period.

Three separate study periods were conducted. A washout period of seven days was maintained between study periods except in three instances between Study Period II and Study Period III due to menstruation. In those three instances the washout period was 14 days.

A linear plot of observed mean metronidazole plasma concentration versus time for metronidazole+terconazole gel (T1) and metronidazole-only gel (T2) is shown in FIG. 1. The enhanced bioavailability of metronidazole in the presence of terconazole is clearly indicated.

Figure 2:
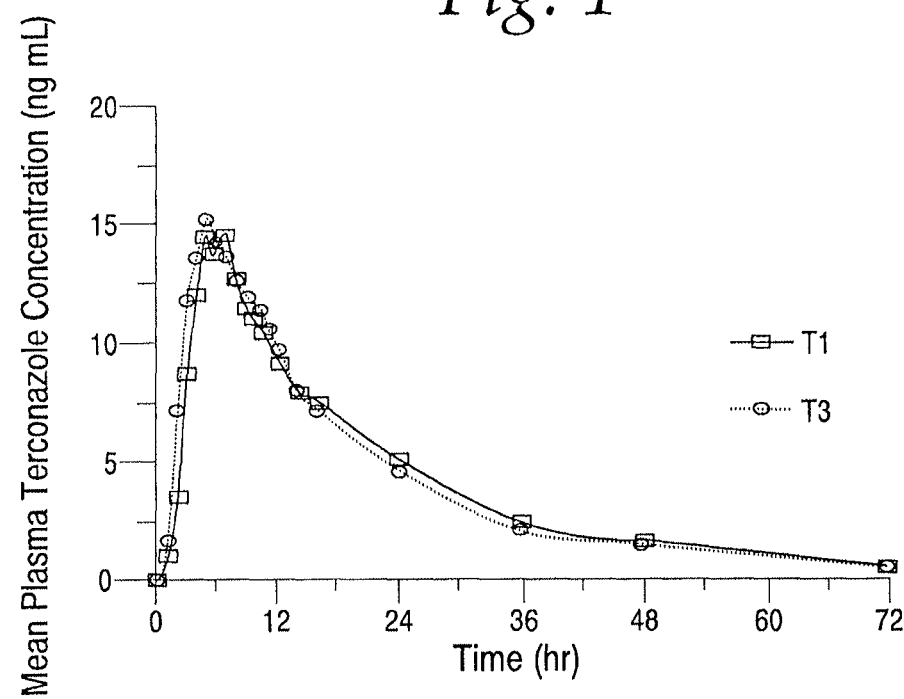
FIG. 2 is a graph showing bioavailability of terconazole alone and in combination with metronidazole in the same gel-like carrier.

FIG. 2 is a linear plot of observed mean terconazole plasma concentration versus time for metronidazole+terconazole gel (T1) and terconazole-only gel (T3) and shows that bioavailability of terconazole is not enhanced by the presence of metronidazole.

Table 2 and 3, below, present the observed pharmacokinetic parameters.

TABLE 2

Metronidazole Bioavailability

| | Mean ± SD (Untransformed Data) | |
|---|---|---|
| Parameter (Unit) | Metronidazole + terconazole gel (T1) (N = 23) | Metronidazole-only gel (T2) (N = 22) |
| $C_{max}$ (ng/mL) | 597.4 ± 167.5 | 348.3 ± 154.3 |
| $AUC_{0-t}$ (hr · ng/mL) | 9286.8 ± 2562.8 | 7371.7 ± 2031.1 |
| $AUC_{0-\infty}$ (hr · ng/mL) | 9396.2 ± 2593.4 | 7463.8 ± 2027.9 |

The above data show that the maximum plasma concentration ($C_{max}$) as well as the area under the curve (AUC) for metronidazole are much greater for metronidazole+terconazole gel ($p<0.001$ for all parameters). Metronidazole bioavailability was significantly enhanced by formulation together with terconazole.

TABLE 3

Terconazole Bioavailability

| | Mean ± SD (Untransformed Data) | |
|---|---|---|
| Parameter (Unit) | Metronidazole + terconazole gel (T1) (N = 23) | Terconazole-only gel (T3) (N = 23) |
| $C_{max}$ (ng/mL) | 18.7 ± 18.4 | 22.1 ± 20.3 |
| $AUC_{0-t}$ (hr · ng/mL) | 285.9 ± 158.5 | 307.0 ± 180.7 |
| $AUC_{0-\infty}$ (hr · ng/mL) | 320.3 ± 156.3 | 320.6 ± 183.2 |

The data in Table 3 show that the bioavailability of terconazole was not significantly influenced by the presence of metronidazole.

The compositions embodying the invention also are more effective than metronidazole alone for curing bacterial vaginosis (BV) infections in women with mixed (concomitant) BV and VVC.

These same three experimental formulations were tested in women who met all clinical and laboratory criteria required to establish a diagnosis of both BV and VVC. Women were given a five-gram applicator full of gel at bedtime for 3 consecutive days. At 7-14 days they were evaluated for clinical cure of both BV and VVC.

BV cure was defined as resolution of abnormal discharge, negative KOH whiff test for amines, and negative for presence of 20% or greater clue cells on examination of vaginal fluid wet mount. In these women with both BV and VVC, it was expected that the metronidazole+terconazole combination would cure significantly more BV than terconazole alone and provide similar cure rates to metronidazole alone for BV. However, the BV cure rate for these women was unexpectedly higher in women who used the metronidazole+terconazole combination gel compared to women who used the metronidazole-only gel as seen below in Table 4

TABLE 4

| BV Clinical Cure in Mixed Infection | Metronidazole + terconazole gel (T1) | Metronidazole-only gel (T2) | Terconazole-only gel (T3) |
|---|---|---|---|
| Number of subjects | 82 | 84 | 83 |
| BV Clinical Cure | 54 (65.9%) | 46 (54.8%) | 38 (45.8%) |
| 95% Confidence Interval | (55.0%, 76.7%) | (43.5%, 66.0%) | (34.5%, 57.1%) |
| Difference: Combination gel minus single-entity gel | | 11.1% | 20.1% |
| p-value (continuity corrected chi-square) | | 0.193 | 0.015 |

BV Cure Rates

VVC cure was defined as resolution of all symptoms and signs attributable to VVC. In these women with both BV and VVC, it was expected that the metronidazole+terconazole combination would cure significantly more VVC than metronidazole alone and provide similar cure rates to terconazole alone for VVC. These expectations were correct, as seen in Table 5 below:

TABLE 5

| VVC Clinical Cure in Mixed Infection | Metronidazole + terconazole gel (T1) | Metronidazole-only gel (T2) | Terconazole-only gel (T3) |
|---|---|---|---|
| Number of subjects | 82 | 84 | 83 |
| VVC Clinical Cure | 53 (64.6%) | 37 (44.0%) | 52 (62.7%) |
| 95% Confidence Interval | (53.7%, 75.6%) | (32.8%, 55.3%) | (51.6%, 73.7%) |
| Difference: Combination gel minus single entity gel | | 20.6% | 2.0% |
| p-value (continuity corrected chi-square) | | 0.012 | 0.918 |

VVC Cure Rates

The invention claimed is:

1. A composition having enhanced bioavailability of metronidazole, a gel-like consistency and comprising metronidazole, terconazole, a physiologically acceptable thickener, and water;
   wherein metronidazole is present in a concentration of at least 0.5 weight percent based on the weight of the composition, terconazole is present in a concentration of at least 0.4 weight percent, based on the weight of the composition, and in an amount sufficient to enhance bioavailability of metronidazole present and the metronidazole is present together with a buffer system which provides a buffered pH value for the composition in the range of 3.75 to 4.25, and metronidazole and terconazole are present in a mole ratio in the range of 3:1 to about 3.5:1.

2. The composition in accordance with claim 1, wherein metronidazole and terconazole are present in a mole ratio of about 3.5:1, respectively.

3. The composition in accordance with claim 1, wherein the amount of metronidazole present in the composition is in the range of about 0.75 weight percent to about 1 weight percent, based on the weight of the composition and the amount of terconazole present in the composition is in the range of about 0.6 weight percent to about 1.2 weight percent, based on the weight of the composition.

4. The composition in accordance with claim 1, wherein metronidazole concentration is about 0.9 weight percent, terconazole concentration is about 0.8 weight percent, the physiologically acceptable thickener is hydroxypropyl methyl cellulose, and the buffer system comprises citric acid and sodium citrate.

5. A method for treating bacterial vaginosis in a human patient which comprises introducing into the vagina of a patient in need of such treatment the composition of claim 1.

* * * * *